US00PP24404P2

(12) United States Plant Patent
Hooijman

(10) Patent No.: US PP24,404 P2
(45) Date of Patent: Apr. 29, 2014

(54) ROSE PLANT NAMED 'ESM R057'

(50) Latin Name: *Rosa hybrida*
Varietal Denomination: ESM R057

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 55 days.

(21) Appl. No.: 13/507,638

(22) Filed: Jul. 13, 2012

(51) Int. Cl.
*A01H 5/00* (2006.01)

(52) U.S. Cl.
USPC ..... Plt./130

(58) Field of Classification Search
USPC ..... Plt./130
See application file for complete search history.

*Primary Examiner* — Annette Para
(74) *Attorney, Agent, or Firm* — C. A. Whealy

(57) ABSTRACT

A new and distinct cultivar of Rose plant named 'ESM R057', characterized by its upright, long and strong flowering stems; vigorous growth habit and high productivity; no thorns; white and light pink-colored flowers that are typically grown as single stems; excellent postproduction longevity; and relative tolerance to Powdery Mildew.

1 Drawing Sheet

Botanical designation: *Rosa hybrida.*
Cultivar denomination: 'ESM R057'.

BACKGROUND OF THE INVENTION

The present Invention relates to a new and distinct cultivar of Rose plant, botanically known as *Rosa hybrida*, which is commercially produced as a cut flower Rose plant and hereinafter referred to by the name 'ESM R057'.

The new Rose plant is a product of a planned breeding program conducted by the Inventor in El Quinche, Pichincha, Ecuador. The objective of the breeding program was to develop new cut flower Rose varieties with unique and attractive flowers and excellent postproduction longevity.

The new Rose plant originated from a cross-pollination made by the Inventor in July, 2006 of a proprietary Rose selection identified as Line 239, not patented, as the female, or seed, parent with a proprietary Rose selection identified as Line 30, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in December, 2007.

Asexual reproduction of the new Rose plant by bud grafting in El Quinche, Pichincha, Ecuador since April, 2008 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype of the new Rose plant may vary somewhat with variations in environmental conditions such as temperature and light intensity, without however, any variance in genotype.

The following traits have been repeatedly observed and are determined to be the unique characteristics of 'ESM R057'.

These characteristics in combination distinguish 'ESM R057' as a new and distinct Rose plant:

1. Upright, long and strong flowering stems.
2. Vigorous growth habit and high productivity.
3. No thorns.
4. White and light pink-colored flowers that are typically grown as single stems.
5. Excellent postproduction longevity.
6. Relative tolerance to Powdery Mildew.

Plants of the new Rose differ from plants of the female parent selection in the following characteristics:

1. Plants of the new Rose are more vigorous than plants of female parent selection.
2. Plants of the new Rose have larger flowers than plants of female parent selection.
3. Plants of the new Rose and the female parent selection differ in flower color as plants of the female parent selection have coral pink-colored flowers.

Plants of the new Rose differ from plants of the male parent selection in the following characteristics:

1. Plants of the new Rose are more vigorous than plants of the male parent selection.
2. Plants of the new Rose have no thorns whereas plants of male parent selection have thorns.
3. Plants of the new Rose have larger flowers than plants of the male parent selection.
4. Plants of the new Rose and the male parent selection differ in flower color as plants of the male parent selection have pink-colored flowers.

Plants of the new Rose can be compared to plants of Rose 'Charming Unique', not patented. In side-by-side comparisons conducted in El Quinche, Pichincha, Ecuador, plants of the new Rose differed from plants of 'Charming Unique' in the following characteristics:

1. Plants of the new Rose were more vigorous than plants of 'Charming Unique'.
2. Plants of the new Rose had stronger flowering stems than plants of 'Charming Unique'.
3. Plants of the new Rose had no thorns whereas plants of 'Charming Unique' had thorns.

4. Plants of the new Rose had larger leaflets than plants of 'Charming Unique'.
5. Plants of the new Rose flowered later than plants of 'Charming Unique'.
6. Plants of the new Rose had larger flowers with more petals per flower than plants of 'Charming Unique'.
7. Plants of the new Rose and 'Charming Unique' differed in flower color as plants of 'Charming Unique' had light red-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of typical flowering stem of 'ESM R057'.

The photographs at the lower left and upper right of the sheet are close-up views of typical flowers of 'ESM R057'.

The photographs at the bottom right of the sheet are close-up views of the upper and lower surfaces of typical leaves of 'ESM R057'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched about 13 to 14 weeks after planting. Plants were 78 weeks old when the photographs and detailed description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R057'.

Parentage:

*Female, or seed, parent.*—Proprietary seedling selection of *Rosa hybrida* identified Line 239, not patented.

*Male, or pollen, parent.*—Proprietary seedling selection of *Rosa hybrida* identified Line 30, not patented.

Propagation:

*Type.*—By bud grafting.

*Time to initiate roots.*—About seven to ten days at 26° C. to 30° C.

*Time to produce a rooted young plant.*—About four to five weeks at 22° C. to 26° C.

*Root description.*—Fibrous, thin to medium in thickness; close to N199B in color.

*Rooting habit.*—Moderately freely branching; sparse to medium density.

Plant description:

*Plant and growth habit.*—Perennial shrub; upright, long and strong flowering stems; typically grown as a single-stem cut flower; vigorous growth habit.

*Branching habit.*—Freely basal branching habit; highly productive with about 9.6 flowering stems developing per plant per year.

*Plant height.*—About 125 cm.

*Plant width (spread).*—About 45 cm.

*Lateral branches (peduncles).*—Length: About 78 cm. Diameter: About 7 mm. Internode length: About 5.9 cm. Texture: Smooth, glabrous; older stems, woody. Color: Close to 146A tinted with close to N199B. Thorns: None observed.

Foliage description:

*Arrangement.*—Alternate; compound with typically five to seven leaflets per leaf.

*Leaf length.*—About 16.9 cm.

*Leaf width.*—About 10 cm.

*Terminal leaflet length.*—About 7.3 cm.

*Terminal leaflet width.*—About 4.6 cm.

*Lateral leaflet length.*—About 6.1 cm.

*Lateral leaflet width.*—About 4 cm.

*Leaflet shape.*—Ovate.

*Leaflet apex.*—Acute.

*Leaflet base.*—Attenuate.

*Leaflet margin.*—Serrate.

*Leaflet texture, upper and lower surfaces.*—Smooth, glabrous; coriaceous.

*Leaflet venation pattern.*—Pinnate.

*Leaflet color.*—Developing leaflets, upper surface: Close to 139A; towards the margins, close to N77A. Developing leaflets, lower surface: Close to 146B tinted with close to 177A. Fully expanded leaflets, upper surface: Between 139A and 147A; venation, close to 147C. Fully expanded leaflets, lower surface: Close to 147B; venation, close to 146C.

*Petioles, leaves.*—Length: About 1.5 cm. Diameter: About 2 mm. Texture, upper surface: Prickly. Texture, lower surface: Smooth, glabrous. Color, upper surface: Close to 146C tinted with close to N199A. Color, lower surface: Between 144A and 146A.

*Petioles, leaflets.*—Length: About 2.8 cm. Diameter: About 2 mm. Texture, upper surface: Prickly. Texture, lower surface: Smooth, glabrous. Color, upper surface: Close to 146A tinted with close to N199C. Color, lower surface: Close to 146A to 146C.

*Stipules.*—Arrangement and appearance: Two, adnate to the petiole, leafy in appearance. Length: About 3 cm. Width: About 3 mm. Shape: Roughly deltoid. Apex: Acuminate. Base: Truncate. Margin: Serrate; glandular, pubescent. Texture, upper and lower surfaces: Smooth, glabrous; membranous. Venation pattern: Pinnate. Color, upper surface: Close to 137A tinted with close to 183A. Color, lower surface: Close to 146A tinted with close to 178A.

Flower description:

*Flower type and flowering habit.*—Symmetrical rosette flowers; flowers typically grown as single stems; flowers face upright.

*Flowering season.*—Plants of the new Rose flower year-round under greenhouse conditions; early flowering habit, plants begin flowering about 73 days after pinching; in the garden, optimal flowering from spring through autumn; flowering intermittent.

*Flower diameter.*—About 14 cm.

*Flower depth (height).*—About 7 cm.

*Flower longevity on plant.*—About 20 days; flowers persistent.

*Flower longevity as a cut flower.*—Excellent postproduction longevity, flowers last about ten to twelve days.

*Fragrance.*—Very faintly fragrant, pleasant.

*Flower buds.*—Shape: Ovoid. Length: About 6.5 cm. Diameter: About 4 cm. Color: Close to 144A tinted with close to 183A.

*Petals.*—Quantity: About 34 per flower; petals imbricate. Length: About 6.7 cm. Width: About 7.3 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Center, close to 39A; towards the margin, close to 159B; towards the base, between 154B and 1C. When opening, lower surface: Center, between 39D and N170D; towards the margin, close to 159C; towards the base, between 154C and 1D. Fully opened, upper surface: Center, close to 43D; towards the margin, close to N155C; towards the base, close to 157C. Fully opened, lower surface: Center, close to 49C; towards the margin, close to N155D; towards the base, close to 157B.

*Petaloids.*—Quantity: About three; petaloids whorled. Length: Variable. Width: Variable. Shape: Irregularly shaped. Apex: Blunt to shortly acute. Base: Obtuse. Margin: Entire or uneven. Texture, upper and lower surfaces: Smooth, glabrous; papery to coriaceous. Color: When opening and fully opened, upper surface: Combination of close to 160A, 33D and 41D. When opening and fully opened, lower surface: Combination of close to 160A, 159C and 29D.

*Sepals.*—Quantity per flower: Typically five in a single whorl. Length: About 5.5 cm. Width: About 1.7 cm. Shape: Roughly deltoid. Apex: Tapered. Base: Truncate. Margin: Entire; glandular and ciliate. Texture, upper and lower surfaces: Leathery. Color: When opening, upper surface: Close to 146A to 146D tinted with close to 187B. When opening, lower surface: Close to 146A tinted with close to 183A. Fully opened, upper surface: Close to 146A; towards the base, close to 146D; central spot, close to N199A. Fully opened, lower surface: Between 146A and 144B.

*Reproductive organs.*—Stamens: Quantity: About 135 per flower. Anther length: About 3 mm. Anther shape: Reniform. Anther color: Close to 163B and 157A. Filament color: Close to 1C. Pollen amount: Abundant. Pollen color: Close to 163C. Pistils: Quantity: About 287 per flower. Pistil length: About 1.6 cm. Stigma shape: Broadly reniform. Stigma color: Close to 1C. Style length: About 1.1 cm. Style color: Close to 53D and 1D. Receptacle height: About 1.7 cm. Receptacle diameter: About 1.5 cm. Receptacle shape: Cup-shaped. Receptacle texture: Smooth, glabrous. Receptacle color: Close to 144A. Fruits and seeds: Fruit and seed production have not been observed on plants of the new Rose.

Pathogen & pest resistance: Plants of the new Rose have been observed to be relatively tolerant to Powdery Mildew. Plants of the new Rose have not been observed to be resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R057' as illustrated and described.

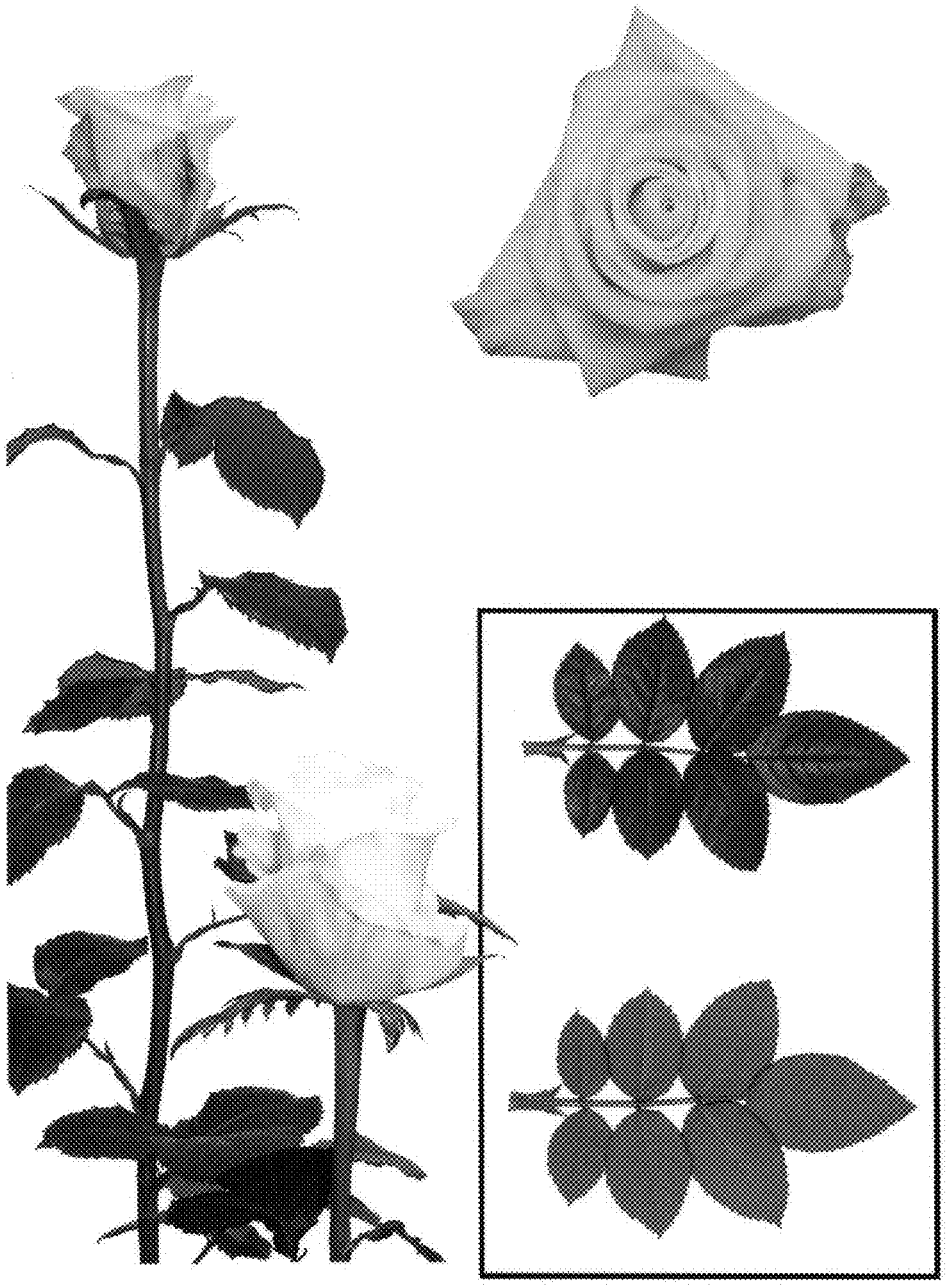

* * * * *